United States Patent
Harttig et al.

(10) Patent No.: US 10,722,651 B2
(45) Date of Patent: Jul. 28, 2020

(54) METHOD FOR PRODUCING A STERILIZED SUBCUTANEOUS ACCESS DEVICE AND A STERILIZED SUBCUTANEOUS ACCESS DEVICE

(71) Applicant: ROCHE DIABETES CARE, INC., Indianapolis, IN (US)

(72) Inventors: Herbert Harttig, Neustadt (DE); Frederic Wehowski, Hockenheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 251 days.

(21) Appl. No.: 15/355,852

(22) Filed: Nov. 18, 2016

(65) Prior Publication Data
US 2017/0065767 A1    Mar. 9, 2017

Related U.S. Application Data

(63) Continuation of application No. PCT/EP2015/060513, filed on May 12, 2015.

(30) Foreign Application Priority Data

May 20, 2014    (EP) .................................... 14169086

(51) Int. Cl.
*A61M 5/172*    (2006.01)
*A61M 5/142*    (2006.01)
(Continued)

(52) U.S. Cl.
CPC .............. *A61M 5/1723* (2013.01); *A61L 2/08* (2013.01); *A61M 5/14248* (2013.01);
(Continued)

(58) Field of Classification Search
CPC ........ A61F 2/00; A61M 31/00; A61M 5/1723
(Continued)

(56) References Cited

U.S. PATENT DOCUMENTS

| 3,230,115 A | 1/1966 | Tamminen |
| 6,503,831 B2 * | 1/2003 | Speakman ................. B41J 2/01 |
| | | 438/674 |

(Continued)

FOREIGN PATENT DOCUMENTS

| CN | 1476566 A | 2/2004 |
| CN | 102065908 A | 5/2011 |

(Continued)

OTHER PUBLICATIONS

Graham, How does radiation effect the electronics of technology, 2011, Naked Science Forum, https://www.thenakedscientists.com/forum/index.php?topic=38360.0 (Year: 2011).*

(Continued)

*Primary Examiner* — Dah-Wei D. Yuan
*Assistant Examiner* — Andrew J Bowman
(74) *Attorney, Agent, or Firm* — Bose McKinney & Evans LLP

(57) ABSTRACT

The application relates to a method for producing a sterilized subcutaneous access device, the method comprising: producing a device carrier unit, comprising providing a carrier, producing a subcutaneous access part on the carrier, the subcutaneous access part being provided with at least one of a sensor device for detecting an analyte present in a bodily fluid and an infusion device for infusion of a substance, and producing an electronic assembly on the carrier, the producing comprising printing a battery on a carrier material, and sterilizing the device carrier unit by radiation sterilization, the sterilizing comprising exposing the printed battery to the radiation applied for sterilization. Furthermore, the application relates to a sterilized subcutaneous access device.

16 Claims, 3 Drawing Sheets

(51) Int. Cl.
*A61L 2/08* (2006.01)
*H01M 2/08* (2006.01)
*H01M 6/40* (2006.01)

(52) U.S. Cl.
CPC ............... *H01M 2/08* (2013.01); *H01M 6/40* (2013.01); *A61L 2202/24* (2013.01); *A61M 2205/8206* (2013.01); *H01M 2220/30* (2013.01)

(58) Field of Classification Search
USPC .................................................. 604/288.01
See application file for complete search history.

(56) References Cited

U.S. PATENT DOCUMENTS

| | | | | |
|---|---|---|---|---|
| 6,561,978 | B1* | 5/2003 | Conn | A61B 5/0031 600/309 |
| 8,864,649 | B2* | 10/2014 | Cahill | A61F 2/0027 600/30 |
| 2002/0040208 | A1* | 4/2002 | Flaherty | A61M 5/14248 604/288.01 |
| 2004/0009398 | A1* | 1/2004 | Dorfman | H01M 4/06 429/217 |
| 2005/0159752 | A1 | 7/2005 | Walker et al. | |
| 2008/0242962 | A1 | 10/2008 | Roesicke et al. | |

FOREIGN PATENT DOCUMENTS

| | | |
|---|---|---|
| CN | 202029145 U | 11/2011 |
| CN | 103127536 A | 6/2013 |
| EP | 2 277 554 A1 | 1/2011 |
| WO | WO 2006/108809 A1 | 10/2006 |
| WO | WO 2011/015659 A1 | 2/2011 |
| WO | WO 2013/136181 A2 | 9/2013 |

OTHER PUBLICATIONS

S1, Sterilization Methods and Their Impact ON Medical Devices Containing Electronics, 2011, Maxim Integrated, pp. 1-9, https://www.maximintegrated.com/en/design/technical-documents/app-notes/5/5068.html (Year: 2011).*

International Preliminary Report on Patentability and Written Opinion of the International Searching Authority, PCT/EP2015/060513, dated May 2, 2016.

National Intellectual Property Administration, P.R. China, Office Action, Application No. 201580039338.0, dated Oct. 26, 2018, 11 pages.

* cited by examiner

METHOD FOR PRODUCING A STERILIZED SUBCUTANEOUS ACCESS DEVICE AND A STERILIZED SUBCUTANEOUS ACCESS DEVICE

RELATED APPLICATIONS

This application is a continuation of PCT/EP2015/060513, filed May 12, 2015, which claims priority to EP 14 169 086.7, filed May 20, 2014, both of which are hereby incorporated herein by reference in their entireties.

BACKGROUND

The present disclosure refers to a method for producing a sterilized subcutaneous access device and a sterilized subcutaneous access device.

Medical devices such as insulin pumps or devices for continuous measurement of an analyte in a bodily fluid, for example, blood glucose or lactate, are operated electrically, and therefore require a power or energy source. The devices may be for use by patients who are not confined to bed, so they must rely on batteries or secondary batteries. The preference is for primary elements, but rechargeable batteries are also usable. For example, document US 2008/0242962 A1 discloses the use of a round cell battery.

In document U.S. Pat. No. 6,561,978 B1 flexible printed batteries known as such for decades (see, for example, U.S. Pat. No. 3,230,115) are proposed for use in medical devices. A continuous sensor system using the iontophoresis principle as a method for obtaining samples is disclosed. The use of flexible printed battery is proposed.

Document US 2005/0159752 A1 discloses the use of sterile battery packs with chemistry based on lithium/manganese dioxide.

When standard commercial batteries or rechargeable batteries are used, a device must be adapted to the standardized geometries of available cells during its development, and suitable contacting solutions must be created that exert sufficient force on the cells to guarantee reliable contact. Consequently, the contacts, and the housing that supports them, must be made from materials that are stiff enough to ensure a prolonged shelf life. Both requirements are complex, and require installation space that is difficult to reconcile with miniaturization.

Document US 2002/040208 A1 discloses a system for delivering fluid to a patient, including a fluid delivery device having a dispenser for causing fluid from a reservoir to flow to an exit port assembly, a local processor connected to the dispenser and programmed to cause fluid flow to the exit port assembly based upon flow instructions, and a local communication element connected to the local processor. A remote control device is separate from the fluid delivery device and includes a remote processor, user interface components connected to the remote processor, and a remote communication element connected to the remote processor and adapted to communicate with the local communication element of the fluid delivery device such that information can be transferred between the local processor and the remote processor. The system also includes at least one data collection assembly adapted to at least one of measure, monitor, calculate, and store a physiologic parameter of a patient.

In document WO 2013/136181 A2 some embodiments have a pump assembly mounted to or supported by a dressing for reduced pressure wound therapy. The dressing can have visual pressure, saturation, and/or temperature sensors to provide a visual indication of the level of pressure, saturation, and/or temperature within the dressing. Additionally, the pump assembly can have a pressure sensor in communication with the flow pathway through the pump, and at least one switch or button supported by the housing, the at least one switch or button being accessible to a user and being in communication with the controller. The pump assembly can have a controller supported within or by the housing, the controller being configured to control an operation of the pump. The pump can be configured to be sterilized following the assembly of the pump such that all of the components of the pump have been sterilized.

In document EP 2 277 554 A1 a radiation sterilization method of a disposable medical device and a manufacturing method are provided, the method comprising the steps of packaging a disposable medical device, which has applied thereto a hydrophilic polymer coating, with a gas permeable packaging material, controlling a product moisture content of the thus packaged medical device by maintaining the device in a given humidity atmosphere for not less than a time at which an equilibrated moisture content is reached, and subjecting, to radiation sterilization, the medical device whose product moisture content has been controlled, so that an eluted matter is reduced in amount and a sliding performance is ensured according to the radiation sterilization method of the hydrophilic polymer-coated, disposable medical device and the manufacturing method.

Document WO 2011/015659 A1 discloses a base part for a medication delivery device. The base part is during use fastened to a patient's skin and connected to a cannula part which cannula part is positioned at least partly subcutaneous. The base part is also connected to a sensor unit which can detect one or more components, e.g., glucose content in the patient's blood. The base part comprises fastening means which fastening means releasably attach the reservoir/delivery part to the base part during use and a first fluid path or means corresponding to a first fluid path from a reservoir permitting a flow of fluid between the reservoir/delivery part and the base part when the reservoir/delivery part is attached to the base part, the first fluid path comprises means for interrupting the fluid flow when the detachable reservoir/delivery part is not attached to the base part and opening the fluid path when the delivery part is attached to the base part. The base part also comprises a lower mounting surface and one or more openings through which two or more subcutaneous units in the form of at least one cannula and at least one sensor part or at least two cannulas extend and it comprises a second fluid path permitting a flow of fluid from the outlet of the first fluid path to an inlet of a subcutaneously positioned cannula during use, and a signal path is provided from the reservoir/delivery part to a sensor contact part. The base part is characterized in that the second fluid path is in fluid connection with an end opening of a subcutaneously positioned cannula during use.

In document WO 2006/108809 A1 a medical device is provided comprising a transcutaneous device unit and a process unit. The transcutaneous device unit may comprise a transcutaneous device for transporting a fluid through a skin portion of a subject, and a mounting surface adapted for application to the skin of the subject. The process unit may comprise a reservoir adapted to contain a fluid drug, the reservoir comprising an outlet means allowing the transcutaneous device to be arranged in fluid communication with an interior of the reservoir, and an expelling assembly for expelling a fluid drug out of the reservoir and through the skin of the subject via the transcutaneous device. The transcutaneous device unit and the process unit further comprise coupling means allowing the reservoir unit to be secured to the transcutaneous device unit in the situation of use. By this arrangement a two-unit system is provided which can be used in a convenient and cost-effective manner.

SUMMARY

This disclosure provides a method for producing a sterilized subcutaneous access device and a sterilized subcutaneous access device by which preparation and use of subcutaneous access devices is simplified.

According to one aspect, a method of producing a sterilized subcutaneous access device is provided. The method comprises producing a device carrier unit. The producing comprises providing a carrier. On the carrier a subcutaneous access part is produced, the subcutaneous access part being provided with at least one of a sensor device for detecting an analyte present in a bodily fluid and an infusion device for infusion of a substance. Also, on the carrier an electronic assembly is produced by printing a battery on a carrier material of the carrier unit. The device carrier unit as whole is sterilized by radiation. In the process of applying the radiation for sterilization, the printed battery is exposed to the radiation applied.

According another aspect, a sterilized subcutaneous access device is provided. The sterilized subcutaneous access device comprises a device carrier unit carrying a subcutaneous access part. The subcutaneous access part is provided as a sterilized part and comprises at least one of a sensor device for detecting an analyte present in a bodily fluid and an infusion device for infusion of a substance or an active component such as a pharmaceutical active substance, e.g., insulin. The device carrier unit is further carrying an electronic assembly which is also sterilized. The electronic assembly may functionally connect to the subcutaneous access part. For example, the electronic assembly may be electrically connected to the sensor device for receiving electric signals. The electronic assembly comprises a printed battery printed on a carrier material. The printed battery is radiation sterilized together with the subcutaneous access part and the electronic assembly.

The printed battery and optionally other parts of the device carrier unit, e.g., other parts of the electronic assembly, are free of radiation shielding not being part of the subcutaneous access device as such. Such specific shielding has to be distinguished from a potential cover of the battery provided for the purpose of establishing battery functionality as such. Also, at least with respect to the printed battery, there is no temporary shielding provided during application of the radiation for sterilization.

The electronic assembly may comprise at least one of semiconductor devices, such as an integrated circuit, and non-semiconductor devices, for example, one or more resistors.

The subcutaneous access part may be configured for continuous subcutaneous access, e.g., for continuously measuring an analyte in a bodily fluid in a human or animal body. As an alternative or in addition, the subcutaneous access part may be configured for continuously applying an infusion to a human or animal body.

The radiation sterilization may be done in a sterilization chamber of a sterilization device different types of which are known as such.

The sterilizing may comprise shielding a part of the electronic assembly not comprising the printed battery from the radiation applied for sterilization. For example, one or more semiconductor devices being part of the electronic assembly may be prevented from exposure of radiation applied for sterilization.

The shielding may comprise permanently shielding the part of the electronic assembly not comprising the printed battery by a radiation shielding device provided on the carrier unit. The radiation shielding device may be provided for the sole purpose of radiation shielding. As an alternative or in addition, there may be a shielding not permanently provided to the device carrier unit, but during the radiation sterilization only. For example, a shielding plate overlaying the part to be shielded may be provided permanently or not permanently in the sterilization chamber.

The printed battery may be provided on a device carrier unit part made of a flexible material. The flexible material may be a foil or a plastic film material. A flexible material on which the printed battery is provided may be a carrier material for the device carrier unit as whole.

The printed battery may be covered with a cover layer. The cover layer may be produced as a single layer or a stack of sub-layers. It may be provided as a foil material. The cover layer may be a sealing layer protecting the printed battery against environmental damage. The cover layer may be not permeable for fluids.

In an embodiment, the printed battery is provided outside a device housing in which part of the electronic assembly is received. As an alternative, the printed battery at least in part may be provided inside the device housing. For the different embodiments, the device housing may be made of a plastic material. The housing may comprise only a single part or may be provided as a multipart housing.

The printed battery may at least partially be surrounding the device housing. The area in which the printed battery is provided may encircle the device housing completely or in part. As an alternative, the printed battery may be provided on opposite sides of the device housing only.

The printed battery may be provided on a device carrier unit flange. The device carrier unit flange may be provided with a flat configuration on a bottom side. The flange part on which the printed battery is provided may be to be adhered to a skin surface when the sterilized subcutaneous access device is in use. The device carrier unit flange, in use, may be provided in plane contact with the skin of human or animal body. The flange part may be provided on a carrier material, for example, a foil, of the device carrier unit.

In a further embodiment, the printed battery is provided on an adhesive patch part of the device carrier unit. The adhesive patch part may extend over the whole bottom of the device carrier unit. The adhesive patch part may provide for at least two functionalities, namely receiving the printed battery and providing adherence to the body skin. The adhesive patch part may be provided on the carrier material of the device carrier unit.

The printed battery may be connected to another part of the electronic assembly by one or more printed conductor paths. The one or more printed conductor paths may be made of carbon paste or metal paste. Different methods may be applied for printing the conductor paths such as a silk screen process or laser transfer printing.

With respect to the method of production, the sterilizing of the device carrier unit may comprise applying electron radiation. In an embodiment, an amount of energy of about 5 to 15 MeV, preferably an amount of energy of about 10 MeV may be applied for radiation sterilization. A dose of about 20 to 30 kGy, preferably 25 kGy may be applied.

Further with respect to the method of production, the printing of the battery may comprise at least one of printing of one or more conductor paths and printing an antenna device. The conductor path and the antenna may be made of different conducting material.

The battery may be produced as a zinc-manganese dioxide battery. The printed battery may be provided with at least one battery type selected from the following group: alkali-manganese battery, lithium-sulphur dioxide battery, lithium-carbon monofluoride battery, lithium-iron sulphide battery, lithium-manganese dioxide battery, lithium-thionyl chloride battery, nickel-oxyhydroxide battery, silver oxide-zinc battery, zinc-carbon battery, zinc-air battery, and rechargeable secondary cells such as nickel-cadmium rechargeable battery, nickel-iron rechargeable battery, nickel-lithium rechargeable battery, nickel-metal hydride rechargeable battery, nickel-zinc rechargeable battery, and lithium-iron phosphate rechargeable battery.

The sensor device may comprise at least one of a blood glucose sensor and a blood lactate sensor for in-vivo blood glucose measurement. The sensor may be configured for continuously measuring at least one of the blood glucose level and the blood lactate level.

The subcutaneous access part and the electronic assembly may be part of an infusion pump carried by the device carrier unit. The infusion pump may comprise an infusion needle. For example, the infusion pump may be configured for infusion of a pharmaceutical active component, e.g., insulin.

With respect to the subcutaneous access device, the embodiments described with reference to the method of producing may apply accordingly.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following description. Rather, the embodiments are chosen and described so that others skilled in the art may appreciate and understand the principles and practices of this disclosure.

Figure 1:
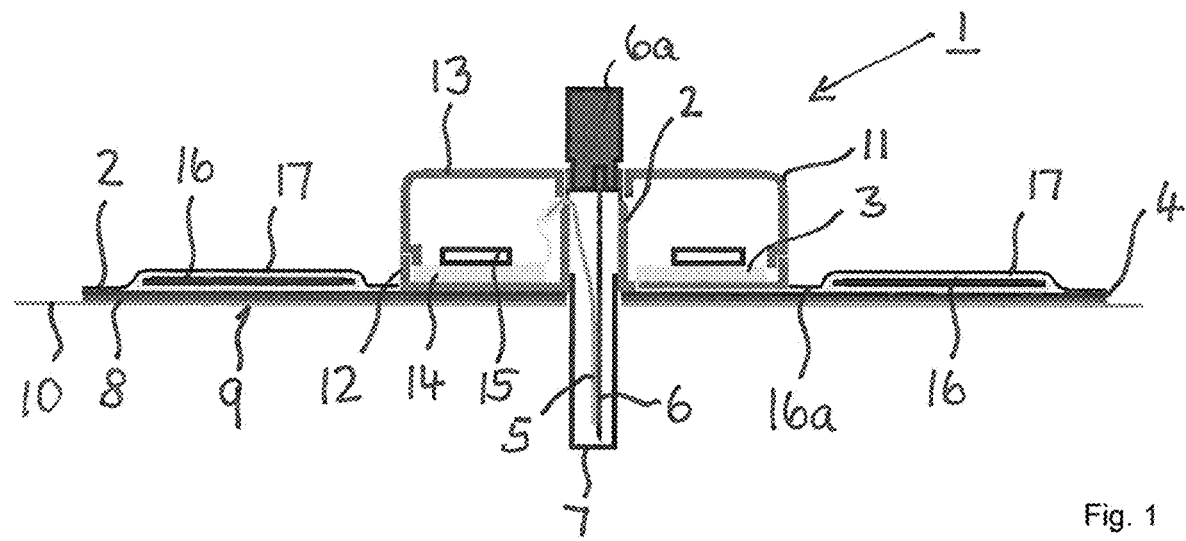
FIG. 1 is a schematic representation of a subcutaneous access device comprising a subcutaneous access part provided with a sensor device.

FIG. 1 shows a schematic representation of a subcutaneous access device 1 comprising a subcutaneous access part 2 and an electronic assembly 3 both provided on a device carrier unit 4. The subcutaneous access part 2 comprises a sensor device 5 combined with an application needle 6 both covered by a protection element 7. The electronic assembly 3 has at least one of semiconductor devices, such as an integrated circuit, and non-semiconductor devices, for example, one or more resistors.

The subcutaneous access device 1 is provided with a liner 8 and a layer 9 of adherence material provided on the bottom of a patch foil 10. On the top side of the patch foil 10 a device housing 11 is provided. The housing 11 comprises a lower housing part 12 and an upper housing part 13.

Within the device housing 11 there are a printed circuit board 14 and electronic devices 15 being part of the electronic assembly 3.

According to the embodiment in FIG. 1, a printed battery 16 is provided as part of the electronic assembly 3 on the patch foil 10 outside the device housing 11. The printed battery 16 is provided on both sides of the device housing 11 according to FIG. 1. For encapsulation, there is a covering or sealing layer 17 overlaying the printed battery 16. The covering or sealing layer 17 may be impermeable with respect to at least one of moisture and liquid. The process of printing a battery may involve, in addition, printing circuit or conductor paths. Such circuit paths may be produced from carbon paste or a metallic paste. A preferred printing method is the silkscreen process. Alternatively, laser transfer printing may be used.

The circuit paths for an antenna or other circuit paths may also be printed at the same time as the printing of circuit paths for contacting the printed battery 16 is done. An antenna may be provided for contactless data communication between the subcutaneous access device and other devices, for example, a control unit or a reading unit. The distance over which this communication takes place may range from a few Millimeters (e.g., NFC=Near Field Communication) to several Meters (e.g., Bluetooth). Such printed antenna, optionally also as an accessory, may be configured for contactless charging of a rechargeable printed battery.

Conductor paths 16a which may be provided as printed conductor paths connect the printed battery 16 which the printed circuit 14 and/or the electronic devices 15 inside the device housing 11.

For coupling of external devices (not shown) to the needle 6, a needle shaft 6a is provided.

The subcutaneous access device 1 shown in FIG. 1 provides for detecting an analyte in bodily fluid by the sensor 5. The needle 6 is provided for penetrating the patient's skin for subcutaneous access of the sensor 5.

For sterilization the subcutaneous access device 1 is located in a sterilization chamber of a sterilization device (not shown). The process of sterilization by radiation as such is known, for example, from document US 2013/0137950 A1.

Figure 2:
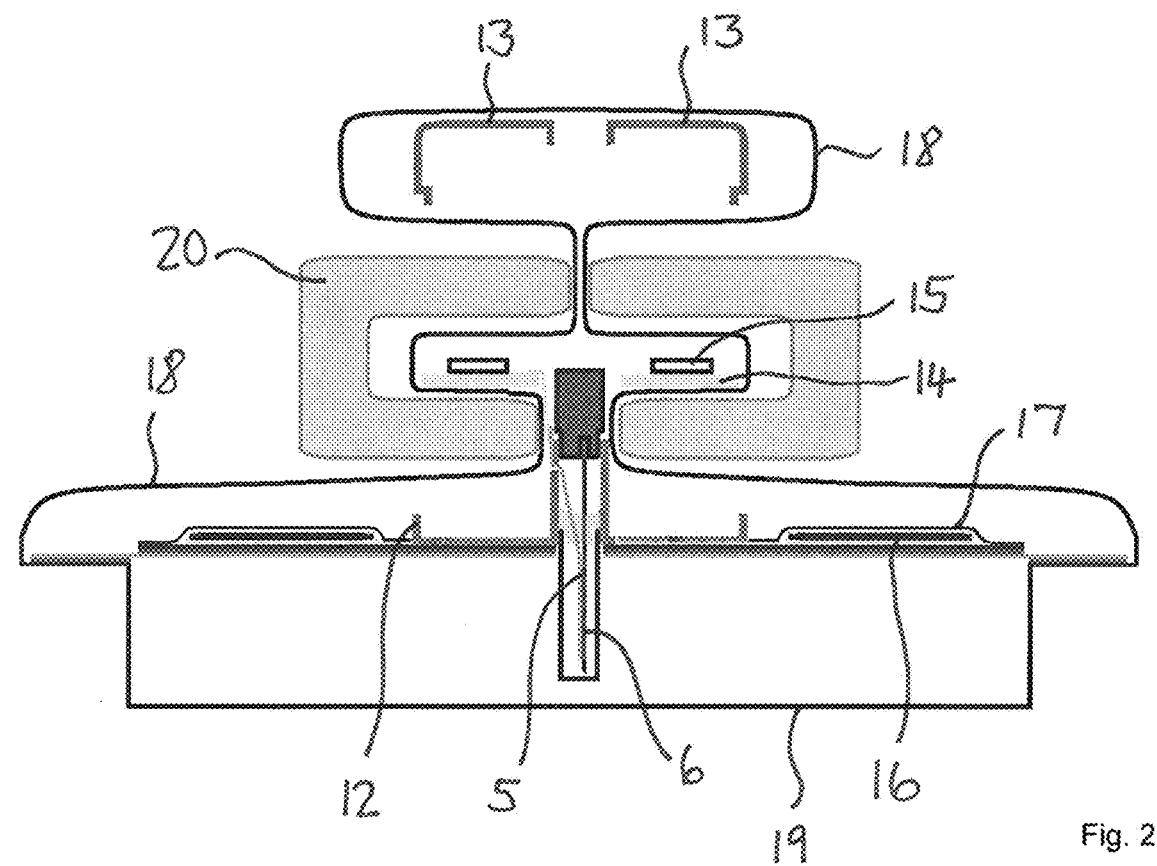
FIG. 2 is a schematic representation of the subcutaneous access device from FIG. 1.

FIG. 2 shows subcutaneous access device 1 covered by a cover or envelope 18 made of a flexible material, for example, a plastic foil. On the bottom the subcutaneous access device 1 is covered by a bottom cover 19 which also may be made of a plastic material. Together, the cover or envelope 18 and the bottom cover 19 provide for a sterilized wrapping of the subcutaneous access device 1.

Referring to FIG. 2, the upper housing part 13 and also the printed circuit board 14 and the electronic devices 15 both being part of the electronic assembly 3 are separated from the lower housing part 12 and covered by a shielding 20. The shielding 20 protects the printed circuit board 14 and the electronic devices 15 from radiation applied for sterilization. After the sterilization is finished, the parts separated from the lower housing part 12 can be placed back again, the cover 18 securing the sterilized conditions.

Figure 3:
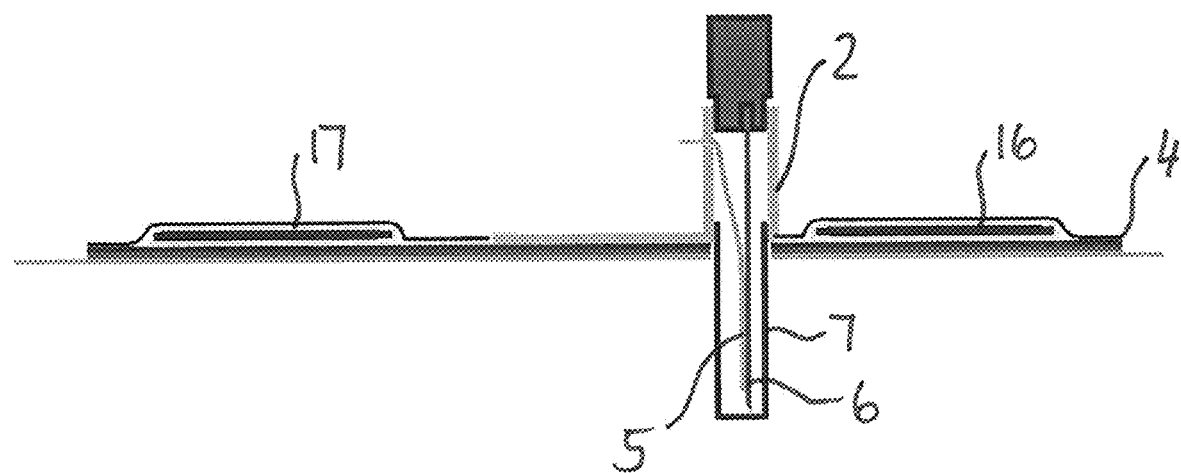
FIG. 3 is a schematic representation of a remaining part of another subcutaneous access device comprising a subcutaneous access part provided with a sensor device.
Figure 4:
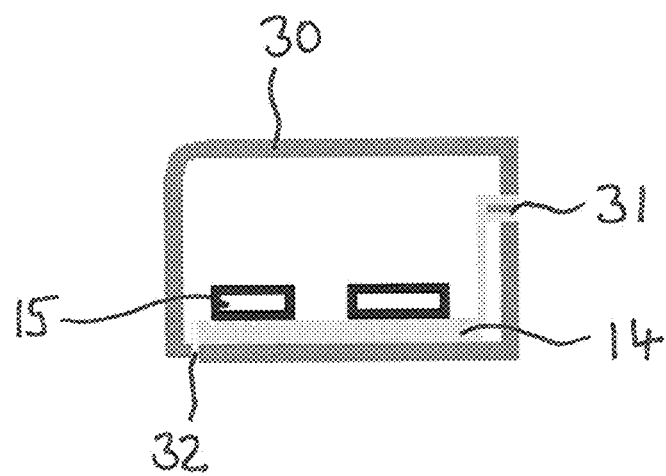
FIG. 4 is a schematic representation of housing part separated from the remaining part of FIG. 3.
Figure 5:
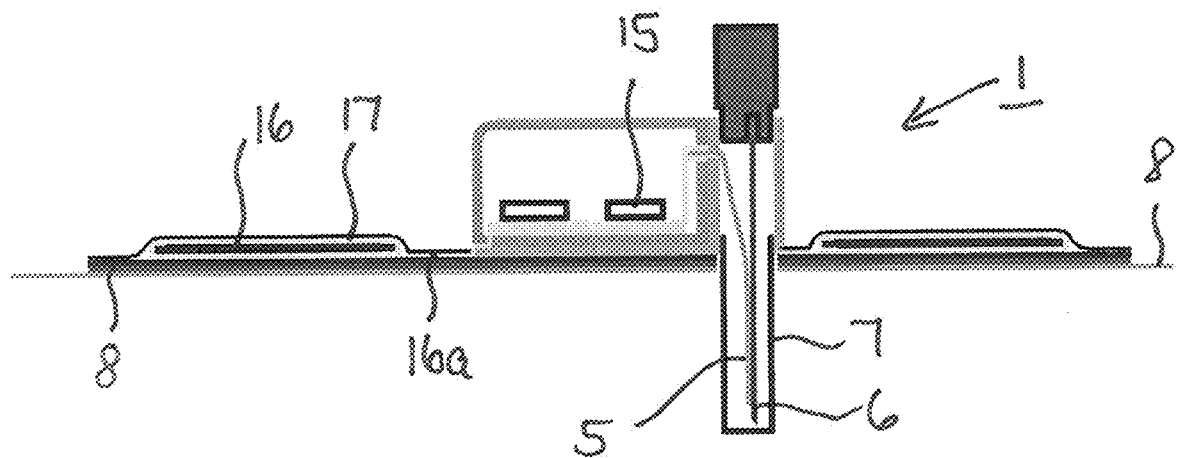
FIG. 5 is a schematic representation of the other subcutaneous access device, wherein the housing part of FIG. 4 and the remaining part of FIG. 3 are assembled.

Referring to FIGS. 3 to 5, a schematic representation of another subcutaneous access device 1 is shown. Again, the electronic assembly 3 may comprise at least one of a semiconductor device, such as an integrated circuit, and a non-semiconductor device, for example, one or more resistors. A housing part 30 receiving part of the electronic assembly 3, namely the printed circuit board 14 and the electronic devices 15, is separable from the device carrier unit 4. The housing part 30 may be taken off for radiation sterilization (see FIG. 4). A connector 31 is provided for connecting the electronic assembly 3 to the sensor 6. There is another connector 32 which may be provided with a connector pad for connecting the printed circuit board 14 and/or the electronic devices 15 to the printed battery 13. After finishing sterilization the subcutaneous access device 1 can be assembled as shown in FIG. 5.

Figure 6:
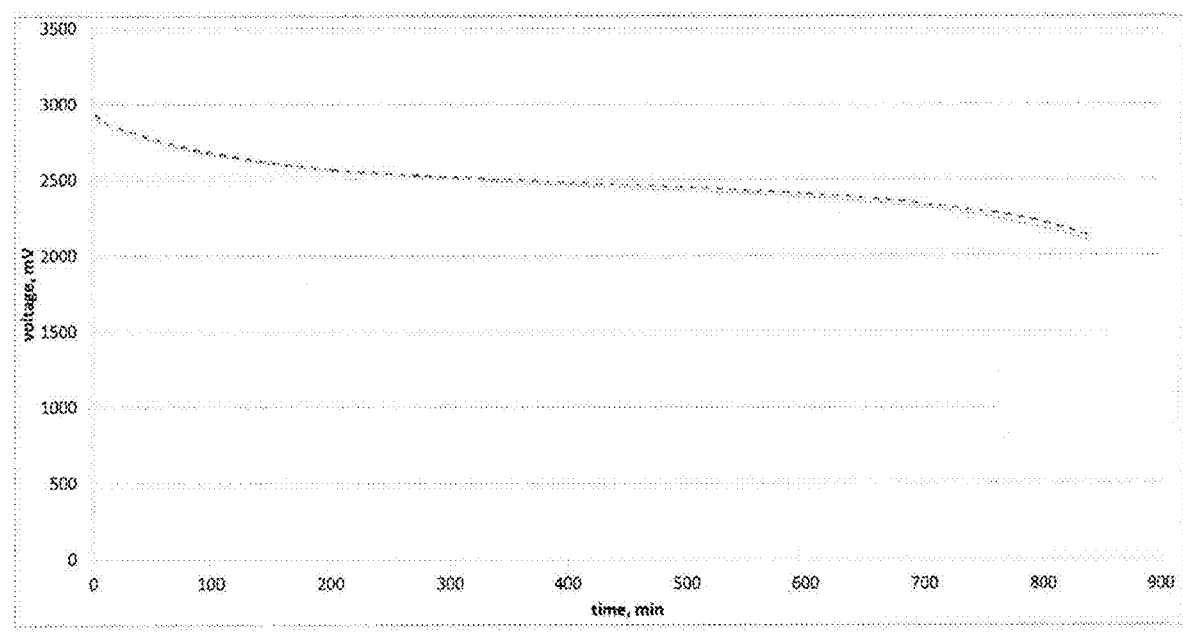
FIG. 6 is a graphical representation of measured electrical potential in dependence on time for a zinc-manganese dioxide cells being sterilized by electron radiation.

FIG. 6 shows a graphical representation of the measured electrical potential in dependence on time for zinc-manganese dioxide cells being sterilized by electron radiation. Results for cells are depicted before and after radiation sterilization by solid and broken lines, respectively.

Sterilization with electron radiation was performed in a flowthrough process. The energy applied for sterilization was 10 MeV, the dosage was 25 kGy. Printed battery in aluminum-laminated Polyethylene foil were packed one layer deep in corrugated cardboard boxes and conveyed through the irradiation unit for sterilization. The temperature in the irradiation unit was kept below 45° C. The corrugated cardboard boxes provide for transportation means only.

Surprisingly, the printed battery with a zinc-manganese dioxide chemistry and zinc chloride as the electrolyte made it possible to carry out radiation sterilization without any loss of performance in terms of voltage and capacitance.

As is shown in FIG. 6, there is no difference between the discharge curves of unsterilized and sterilized battery. The batteries used were Reg 3.0 V Enfucell Softbattery® manufactured by Enfucell Oy, Vantaa, Finland, with a capacitance of 10 mAh. Discharging was carried out across a resistor with 3.0 kΩ+–1%. Voltage values were recorded once a minute.

In conclusion, the printed battery can be sterilized as part of the subcutaneous access device without being protected by shielding against the radiation applied for sterilization.

Other types of battery with different chemistry may be applied: alkali-manganese battery, lithium-sulphur dioxide battery, lithium-carbon monofluoride battery, lithium-iron sulphide battery, lithium-manganese dioxide battery, lithium-thionyl chloride battery, nickel-oxyhydroxide battery, silver oxide-zinc battery, zinc-carbon battery, zinc-air battery, or in rechargeable secondary cells such as nickel-cadmium rechargeable battery, nickel-iron rechargeable battery, nickel-lithium rechargeable battery, nickel-metal hydride rechargeable battery, nickel-zinc rechargeable battery, lithium-iron phosphate rechargeable battery or variants thereof.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A method for producing a sterilized subcutaneous access device, comprising:
   producing a device carrier unit, comprising:
   providing a carrier;
   producing a subcutaneous access part on the carrier, the subcutaneous access part having at least one of a sensor device for detecting an analyte present in a bodily fluid and an infusion device for infusion of a substance; and
   producing an electronic assembly on the carrier, the producing comprising printing a battery on a carrier material; and
   sterilizing the device carrier unit by radiation, the sterilizing comprising exposing the printed battery to the radiation applied for sterilization and shielding a part of the electronic assembly from the radiation applied for sterilization; and
   wherein the printed battery has a zinc-manganese dioxide chemistry with zinc chloride as the electrolyte and has a discharge curve after being sterilized by radiation that is without significant loss of performance relative to a discharge curve of the printed battery before being sterilized.

2. Method according to claim 1, wherein the shielding comprises permanently shielding the part of the electronic assembly by a radiation shielding device provided on the carrier unit.

3. Method according to claim 1, wherein the producing comprises producing the printed battery on a device carrier unit part made of a flexible material.

4. Method according to claim 1, wherein the producing comprises covering the printed battery with a cover layer.

5. Method according to claim 1, wherein the producing comprises providing the printed battery outside a device housing in which part of the electronic assembly is received.

6. Method according to claim 5, wherein the printed battery at least partially surrounds a housing of the device carrier unit.

7. Method according to claim 1, wherein the producing comprises providing the printed battery on a device carrier unit flange.

8. Method according to claim 1, wherein the producing comprises providing the printed battery on an adhesive patch part of the device carrier unit.

9. Method according to claim 1, wherein the producing comprises connecting the printed battery to at least one other device of the electronic assembly by one or more printed conductor paths.

10. Method according to claim 1, wherein the sterilizing comprises applying electron radiation.

11. Method according to claim 1, wherein the printing comprises printing an antenna device.

12. Method according to claim 1 wherein the step of producing an electronic assembly on the carrier comprises providing the printed battery on an adhesive patch part of the device carrier unit outside of a device housing in which the part of the electronic assembly shielded from radiation is received and wherein the part of the electronic assembly shielded from radiation comprises a printed circuit board.

13. Method according to claim 12 wherein temporary shielding which is not part of the sterilized subcutaneous access device is used to shield the part of the electronic assembly shielded from radiation and wherein the device housing which receives the part of the electronic assembly shielded from radiation is not shielded by the temporary shielding.

14. A method for producing a sterilized subcutaneous access device, comprising:
   producing a device carrier unit, comprising:
   providing a carrier;
   producing a subcutaneous access part on the carrier, the subcutaneous access part having at least one of a sensor device for detecting an analyte present in a bodily fluid and an infusion device for infusion of a substance; and
   producing an electronic assembly on the carrier, the producing comprising printing a battery on a carrier material;
   sterilizing the device carrier unit by radiation, the sterilizing comprising exposing the printed battery to the radiation applied for sterilization and shielding a part of the electronic assembly from the radiation applied for sterilization; and wherein the sterilizing radiation is applied at an energy in the range from 5 to 15 MeV and in a dose of 20 to 30 kGy.

15. Method according to claim 14, wherein the printed battery has a zinc-manganese dioxide chemistry with zinc chloride as the electrolyte and has a discharge curve after being sterilized by radiation that is without significant loss of performance relative to a discharge curve of the printed battery before being sterilized.

16. Method according to claim 12 wherein the sterilizing radiation is applied at an energy in the range from 5 to 15 MeV and in a dose of 20 to 30 kGy.

* * * * *